US005616781A

United States Patent [19]

Sajic et al.

[11] Patent Number: 5,616,781

[45] Date of Patent: Apr. 1, 1997

[54] LIQUID DETERGENT COMPOSITIONS COMPRISING SALTS OF ALPHA SULFONATED FATTY ACID ESTERS AND ANIONIC SURFACTANTS

[75] Inventors: Branko Sajic, Lincolnwood; Irma Ryklin, Buffalo Grove; Brian L. Frank, Arlington Heights, all of Ill.

[73] Assignee: Stepan Company, Northfield, Ill.

[21] Appl. No.: 410,933

[22] Filed: Mar. 27, 1995

Related U.S. Application Data

[63] Continuation of Ser. No. 135,288, Oct. 12, 1993, abandoned.

[51] Int. Cl.$^6$ .......... C07C 323/52

[52] U.S. Cl. .......... 510/221; 510/235; 510/429; 560/147

[58] Field of Search .......... 252/554, 555, 252/556, 557; 560/147

[56] References Cited

U.S. PATENT DOCUMENTS

| | | | |
|---|---|---|---|
| 3,915,903 | 10/1975 | Wise | 252/552 |
| 4,435,317 | 3/1984 | Gerritsen et al. | 252/547 |
| 4,495,092 | 1/1985 | Schmid et al. | 252/559 |
| 4,772,425 | 9/1988 | Chirash et al. | 252/547 |

FOREIGN PATENT DOCUMENTS

| | | |
|---|---|---|
| 949843 | 6/1974 | Canada . |
| 2118560 | 3/1972 | France . |
| 2462474 | 2/1981 | France . |
| 2052881 | 4/1972 | Germany . |
| 2333356 | 1/1975 | Germany . |
| 2416745 | 6/1975 | Germany . |
| 2804324 | 8/1978 | Germany . |
| 50-151905 | 12/1975 | Japan . |
| 51-047007 | 8/1976 | Japan . |
| 52-028507 | 3/1977 | Japan . |
| 53-027603 | 3/1978 | Japan . |
| 53-029314 | 3/1978 | Japan . |
| 55-108496 | 4/1980 | Japan . |
| 58-080394 | 5/1983 | Japan . |
| 58-080395 | 5/1983 | Japan . |
| 58-080396 | 5/1983 | Japan . |
| 59-004699 | 1/1984 | Japan . |
| 59-004697 | 1/1984 | Japan . |
| 59-059797 | 4/1984 | Japan . |
| 59-221392 | 12/1984 | Japan . |
| 59-221394 | 12/1984 | Japan . |
| 59-221395 | 12/1984 | Japan . |
| 59-221399 | 12/1984 | Japan . |
| 62-043500 | 2/1987 | Japan . |
| 62-115096 | 5/1987 | Japan . |
| 04213399 | 2/1992 | Japan . |
| 04202300 | 4/1992 | Japan . |
| WO9206156 | 4/1992 | WIPO . |
| WO9206157 | 4/1992 | WIPO . |

OTHER PUBLICATIONS

Bistline at al., J. Am. Oil Chem. Soc. 49: 63–69 (Feb. 1972). "Soap–Based Detergent Formulations 1. Comparison of Soap–Lime Soap Dispersing Agent Formulations With Phosphate Built Detergents".

Weil and Linfield, J. Am. Oil Chem. Soc. 54: 339–346 (Jun. 1976). "Surface Active Properties of Combinations of Soap and Lime Soap Dispersing Agents".

Smith, Soap/Cosmetics Chemical Specialities 65: 48 (Apr., 1989). "Alpha–Sulfo Methyl Esters A New Alternative".

Weil, et al., Technical 54: 1–3 (Jul. 1977) "The Mutual Solubilization of Soap and Lime Soap Dispersing Agents".

Research Disclosure, Oct. 1989, "Soap/Alpha–Sulfo Methyl Ester Based Liquid Laundry Detergents", pp. 707–709.

Satsuki et al., JAOCS 69:672–677 (Aug. 1992). "Performance and Physicochemical Properties of α–Sulfo Fatty Acid Methyl Esters".

Schambil and Schwuger, Tenside, Surfactants, Deterg. 27(6): 380–5 (Oct. 1990). "Physico–Chemical Properties of α–Sulpho Fatty Acid Methyl Esters and α–Sulpho Fatty Acid Di Salts".

Maurer et al., Technical 50: 287–291 (Sep. 1973) "Biological Behavior of Some Soap–Based Detergents".

Joseph C. Drozd, Proc. World Conf. Oleochem., pp. 256–268 (Mar. 1991) "Use of Sulfonated Methyl Esters in Household Cleaning Products".

*Primary Examiner*—Brian M. Burn
*Attorney, Agent, or Firm*—McDonnell Boehnen Hulbert & Berghoff, Ltd.

[57] ABSTRACT

Disclosed are detergent compositions comprising critical amounts of divalent cations and a minimum amount of a mixture of a salt of alpha-sulfonated methyl ester of a fatty acid, anionic surfactants and foam stabilizing auxiliary surfactants.

4 Claims, No Drawings

LIQUID DETERGENT COMPOSITIONS COMPRISING SALTS OF ALPHA SULFONATED FATTY ACID ESTERS AND ANIONIC SURFACTANTS

This application is a continuation of U.S. patent application Ser. No. 08/135,288, filed Oct. 12, 1993 (now abandoned).

BACKGROUND OF THE INVENTION

1. Field of the Invention

The present invention relates to detergent compositions comprising one or more anionic sulfate or sulfonate surfactants and magnesium. More particularly, the invention relates to detergent compositions comprising a hydrotropic surfactant, at least one primary anionic surfactant, and an auxiliary surfactant. It relates to detergent compositions which possess desirable cleaning and sudsing properties, are mild, and are especially suitable for use in dishwashing applications.

2. Description of the Related Art

The use of anionic sulfated or sulfonated surfactants in detergent compositions is known. However, it would be desirable to incorporate such surfactants into detergent compositions which exhibit improved cleaning and increased amounts of foam stability without the need for a traditional hydrotrope, especially in the presence of grease. Dilute water mixtures of such desired compositions would have longer, improved periods of usability.

The use of anionic sulfate or sulfonate surfactants in detergent compositions is known in the art.

The use of magnesium in detergent compositions is also known in the art. U.S. Pat. 4,435,317 discloses detergent compositions comprising magnesium and anionic alkyl sulfate and alkyl ether sulfate surfactants.

PCT Publication Nos. WO 92/06156 and WO 92/06157 disclose detergent compositions containing anionic surfactants and magnesium salts. The compositions disclosed in those publications require polyhydroxy fatty acid amides in combination with anionic surfactant and a traditional hydrotrope. Compositions as taught in those publications do not have suitable grease-cutting performance and foam stability.

Detergent compositions comprising anionic surfactants at high water dilution, i.e., low concentration of surfactant in water, typically do not provide good cleaning and grease-cutting. This is especially true in hard tap water. In addition, such detergent compositions are normally not clear at the high dilution required for use. Without being bound by a particular theory, it is believed that water-detergent compositions that are clear, i.e., all components are soluble in the composition, at high surfactant dilution will display markedly improved grease-cutting and cleaning. Much effort has been directed to the obtention of anionic surfactant detergent compositions that will be clear when used at high dilution and will therefore provide good cleaning and grease-cutting.

SUMMARY OF THE INVENTION

The present invention provides detergent compositions which exhibit unexpectedly superior cleaning and sudsing performance, ease of rinsing, and lack of "slippery" feel. Certain compositions are particularly mild to the skin.

The present invention provides detergent compositions comprising anionic surfactants that may successfully be used at high water dilution, i.e., low concentration of surfactant in water, to provide good cleaning and grease-cutting.

The present invention further provides detergent compositions that are clear in both the concentrated form and at the high dilution required for use. All the components, including the surfactant components, are substantially soluble in these clear compositions.

The present invention further provides a method for cleaning soiled dishes by treating said dishes with the particular detergent compositions described herein.

The present invention is also directed toward a method for cleaning hard surfaces such as soiled dishes, said method comprising treating the surfaces with the detergent compositions described herein.

Methods are also provided for preparing concentrated liquid detergent compositions suitable for dilution to ready-to-use concentrations any time prior to use.

The invention provides detergent compositions comprising critical amounts of divalent cations and a minimum amount of a mixture of hydrotropic, anionic, and foam stabilizing auxiliary surfactants. In the mixture, the hydrotropic surfactant is an alpha-sulfonated ester of a fatty acid. The anionic surfactant is selected from the group consisting of linear alkyl benzene sulfonates, alkyl sulfates, alkyl ethoxy sulfates, alpha-olefin sulfonates, paraffin sulfonates, alkyl glyceryl ether sulfonates, secondary alkane sulfonates, acyl—N—($C_1$-$C_4$ alkyl) or —N—($C_2$-$C_4$ hydroxyalkyl) glucamine sulfates, $C_8$–$C_{18}$ alkyl sulfoacetates and $C_8$–$C_{18}$ secondary alcohol sulfates and mixtures thereof. In the surfactant mixture, the hydrotropic surfactants and anionic surfactants are normally present at ratios of from about 1:1.5 to about 1:8.

The auxiliary foam stabilizing surfactant is typically an amide, amine oxide, betaine, sultaine, $C_8$–$C_{18}$ fatty alcohol or mixtures thereof.

DETAILED DESCRIPTION OF THE INVENTION

Clear dishwashing liquids and other detergent compositions containing magnesium salts of linear-alkyl benzene sulfonates and alkanolamides are difficult to prepare since such magnesium salts do not appear to be soluble in the final compositions. Traditional aromatic hydrotropes such as sodium xylene sulfonate or sodium cumene sulfonate have normally been used to improve the solubility of dishwashing liquid components and thus yield clear dishwashing liquids. However, because aromatic hydrotropes are merely cloud-point-reducers and have little or no detersive potential, their presence in dishwashing liquids does not improve the performance of the compositions, and frequently reduces the performance.

It has been discovered that when a hydrotropic surfactant which is an alpha-sulfonated alkyl ester of a fatty acid is combined in a detergent composition with an auxiliary surfactant and a primary anionic surfactant at a weight ratio of hydrotropic to primary surfactant of 1:1.5 to 1:8 and a total surfactant amount of from about 32 to 90 percent by weight in the presence of a minimum amount of a divalent cation, the composition demonstrates surprisingly improved cleaning and grease cutting at dilute concentrations.

Moreover, such compositions are unexpectedly clear at both high and low water dilution even when they comprise divalent salts of various anionic surfactants without a traditional hydrotrope.

Thus, the invention comprises detergent compositions which comprise:

(a) a hydrotropic surfactant which is a blend of a mono-salt of an alpha-sulfonated methyl ester of a fatty acid having from 8–20 carbon atoms and a di-salt of .an alpha-sulfonated fatty acid, the ratio of mono-salt to di-salt being at least about 2:1;

(b) an anionic surfactant selected from the group consisting of linear alkyl benzene sulfonates where the alkyl portion has from about 8 to 15 carbon atoms, alkyl sulfate where the alkyl portion has from about 8 to 18 carbon atoms, alkyl ethoxy sulfates where the alkyl portion has from about 8 to 18 carbon atoms and the average degree of ethoxylation is from about 1 to 7, alpha-olefin sulfonates where the olefin portion is a straight or branched chain unsaturated hydrocarbon having from 8 to 24 carbon atoms, paraffin sulfonate having from 8 to 18 carbon atoms, $C_8$–$C_{20}$ alkyl glyceryl ether sulfonates, $C_8$–$C_{18}$ secondary alkane sulfonates, $C_9$–$C_{17}$ acyl-N-($C_1$–$C_4$ alkyl) or -N-($C_2$–$C_4$ hydroxyalkyl) glucamine sulfates, $C_8$–$C_{18}$ alkyl sulfoacetates and $C_8$–$C_{18}$ secondary alcohol sulfates and mixtures thereof;

(c) an auxiliary foam stabilizing surfactant; and (d) a divalent cation selected from the group consisting of $Ca^{++}$ and $Mg^{++}$.

It is important that the amount of hydrotropic and anionic surfactants present in the composition as salts of the divalent cation be at least about 30% by weight of the mixture of surfactants, and can be as much as about 100% by weight of the mixture. I.e., the ratio of moles of divalent cation to the moles of surfactants may range from about 1:3 to 1:1.

The weight ratio of the hydrotropic surfactant to anionic surfactant in the compositions is usually from about 1:1.5 to 1:8, and the amount of the mixture of surfactants in the composition is from about 32 to 90% by weight. When combined in these amounts and at these ratios, the mixture of surfactants and the divalent cation cooperate to substantially permanently maintain all components in solution. In other words, the mixture of surfactants and the divalent cation substantially maintain a clear detergent composition.

In certain embodiments of the invention, the detergent compositions comprise (a) a salt of a alpha-sulfonated methyl ester of a fatty acid having from about 8 to 18 carbon atoms;

(b) a salt of a linear alkyl benzene sulfonate where the alkyl portion has about 8 to 15 carbon atoms;

(c) a foam stabilizing surfactant;

(d) an ammonium salt of an alkoxylated alkyl sulfate where the alkyl group has from about 8 to 18 carbon atoms and has between about 1 and 7 moles of ethoxylation; and (e) a divalent cation where the divalent cation is present at a ratio of moles of divalent cation to total moles of surfactant of from about 1:3 to 1:1.

Hydrotropic Surfactant

By hydrotropic surfactant is meant a compound that simultaneously behaves as (1) a hydrotrope, i.e., a compound with the ability to increase the solubilities of certain slightly water-soluble organic compounds and metal salts of organic compounds, and (2) a surfactant, i.e., a water-soluble compound that reduces the surface tension of liquids, or reduces interfacial tension between two liquids or a liquid and a solid. These hydrotropic surfactants also act as sequesterants for divalent metallic salts and solubilizers for metal salts of organic compounds.

The hydrotropic surfactant of the invention is a blend of a mono-cation salt (mono-salt) of an alpha-sulfonated methyl ester of a fatty acid and a di-cation salt (di-salt) of an alpha-sulfonated fatty acid, the ratio of mono-salt to di-salt being at least about 2:1.

The hydrotropic surfactant compositions is present in the inventive compositions at concentrations of from about 2–30% by weight. Preferred compositions contain about 3–12% by weight hydrotropic surfactant. Most preferred compositions contain about 7–9% by weight hydrotropic surfactant.

The alpha-sulfonated alkyl ester employed in the inventive compositions may be pure alkyl ester or a blend of (1) a mono-salt of an alpha-sulfonated alkyl ester of a fatty acid having from 8–20 carbon atoms where the alkyl portion forming the ester is straight or branched chain alkyl of 1–6 carbon atoms and (2) a di-salt of an alpha-sulfonated fatty acid, the ratio of mono-salt to di-salt being at least about 2:1. The alpha-sulfonated alkyl esters used in the invention are typically prepared by sulfonating an alkyl ester of a fatty acid with a sulfonating agent such as $SO_3$. When prepared in this manner, the alpha-sulfonated alkyl esters normally contain a minor amount, not exceeding 33% by weight, of the di-salt of the alpha-sulfonated fatty acid which results from hydrolysis of the ester. Preferred alpha-sulfonated alkyl esters contain less than about 10% by weight of the di-salt of the corresponding alpha-sulfonated fatty acid.

The alpha-sulfonated alkyl esters, i.e., alkyl ester sulfonate surfactants, include linear esters of $C_8$–$C_{20}$ carboxylic acid (i.e., fatty acids) which are sulfonated with gaseous $SO_3$ according to the "The Journal of American Oil Chemists Society," 52 (1975), pp. 323–329. Suitable starting materials would include natural fatty substances as derived from tallow, palm oil, etc.

The preferred alkyl ester sulfonate surfactants, especially for laundry applications, comprise alkyl ester sulfonate surfactants of the structural formula:

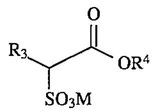

wherein $R_3$ is a $C_8$–$C_{20}$ hydrocarbyl, preferably an alkyl, or combination thereof, $R_4$ is a straight or branched chain $C_1$–$C_6$ hydrocarbyl, preferably an alkyl, or combination thereof, and M is a cation which forms a water soluble salt with the alkyl ester sulfonate. Suitable salt-forming cations include metals such as calcium, magnesium, sodium, potassium, and lithium, and substituted or unsubstituted ammonium cations, such as monoethanol amine, diethanolamine, and triethanolamine. Preferably, $R_3$ is $C_{10}$–$C_{16}$ alkyl, and $R_4$ is methyl, ethyl or isopropyl. More preferred are alpha-sulfonated methyl esters of mixtures of fatty acids having an average of from 12 to 16 carbon atoms. Most preferred are alpha-sulfonated methyl and ethyl esters of mixtures of fatty acids having an average of from about 12 to 14 carbon atoms. A particularly preferred mixture has an average of about 13.6 carbon atoms in the fatty acid portion.

Primary Anionic Surfactant

Primary anionic surfactants can be selected from the following: alkyl benzene sulfonates, alkyl sulfates, alkyl ethoxy sulfates, paraffin sulfonates, monoalkane sulfonates, olefin sulfonates, and alkyl glyceryl sulfonates. The anionic surfactant is present in the detergent at concentrations of from 2–70% by weight.

Alkyl benzene sulfonates useful in compositions of the present invention are those in which the alkyl group, which is substantially linear, contains 8–15 carbon atoms, preferably 10–13 carbon atoms, a material with an average carbon chain length of about 11.5 being most preferred. The phenyl isomer distribution, i.e., the point of attachment of the alkyl chain to the benzene nucleus, is not critical, but alkyl benzenes having a high 2-phenyl isomer content are preferred.

Suitable alkyl sulfates are primary alkyl sulfates in which the alkyl group contains 8–18 carbon atoms, more preferably an average of 12–14 carbon atoms preferably in a linear chain. $C_{10}$–$C_{16}$ alcohols, derived from natural fats, or Ziegler olefin build-up, or OXO synthesis, form suitable sources for the alkyl group. Examples of synthetically derived materials include Dobanol 23 (RTM) sold by Shell Chemicals (UK) Ltd., Ethyl 24 sold by the Ethyl Corporation, a blend of $C_{13}$–$C_{15}$ alcohols in the ratio 67% $C_{13}$, 33% $C_{15}$ sold under the trade name Lutensol by BASF GmbH and Synperonic (RTM) by ICI Ltd., and Lial 125 sold by Liquichimica Italina. Examples of naturally occurring materials from which the alcohols can be derived are coconut oil and palm kernel oil and the corresponding fatty acids.

Alkyl ethoxy sulfate surfactants comprise a primary alkyl ethoxy sulfate derived from the condensation product of a $C_8$–$C_{18}$ alcohol with an average of up to 7 ethylene oxide groups. The $C_8$–$C_{18}$ alcohol itself can be obtained from any of the sources previously described for the alkyl sulfate component. $C_{12}$–$C_{13}$ alkyl ethoxy sulfates are preferred as primary anionic surfactants where the average degree of ethoxylation is about 3.

Conventional base-catalyzed ethoxylation processes to produce an average degree of ethoxylation of 12 result in a distribution of individual ethoxylates ranging from 1 to 15 ethoxy groups per mole of alcohol, so that the desired average can be obtained in a variety of ways. Blends can be made of material having different degrees of ethoxylation and/or different ethoxylate distributions arising from the specific ethoxylation techniques employed and subsequent processing steps such as distillation. In preferred compositions in accordance with the present invention as alkyl ethoxy sulfate is used with has an average degree of ethoxylation of from 0.4 to 6.5, more preferably from 2 to 4.

Paraffin sulfonates are also useful in the present invention and have from 8 to 18 carbon atoms per molecule, more desirably 13 to 16 carbon atoms per molecule. These sulfonates are preferably prepared by subjecting a cut of paraffin, corresponding to the chain length specified above, to the action of sulfur dioxide and oxygen in accordance with the well-known sulfoxidation process. The product of this reaction is a secondary sulfonic acid which is then neutralized with a suitable base to provide a water-soluble secondary alkyl sulfonate. Similar secondary alkyl sulfonates may be obtained by other methods, i.e. by the sulfochlorination method in which chlorine and sulfur dioxide are reacted with paraffins in the presence of actinic light, the resulting sulfonyl chlorides being hydrolyzed and neutralized to form the secondary alkyl sulfonates. Whatever technique is employed, it is normally desirable to produce the sulfonate as the monosulfonate, having no unreacted starting hydrocarbon or having only a limited proportion thereof present and with little or no inorganic salt by-product. Similarly, the proportions of disulfonate or higher sulfonated material will be minimized, although some may be present. The monosulfonate may be terminally sulfonated or the sulfonate group may be joined on the 2-carbon or other carbon of the linear chain. Similarly, any accompanying disulfonate, usually produced when an excess of sulfonating agent is present, may have the sulfonate groups distributed over different carbon atoms of the paraffin base, and mixtures of the monosulfonates and disulfonates may be present.

Mixtures of monoalkane sulfonates wherein the alkanes are of 14 and 15 carbon atoms are particularly preferred wherein the sulfonates are present in the weight ratio of $C_{14}$–$C_5$ paraffins in the range of 1:3 to 3:1.

Olefin sulfonates useful in the present invention are mixtures of alkene-1-sulfonates, alkene hydroxysulfonates, alkene disulfonates and hydroxydisulfonates, and are described in the commonly assigned U.S. Pat. No. 3,332,880, issued to P. F. Pflauner and A. Kessler on Jul. 25, 1967.

Suitable alkyl glyceryl ether sulfonates are those derived from ethers of coconut oil and tallow.

Other sulfate surfactants include the $C_8$–$C_{17}$ acyl-N-($C_1$–$C_4$ alkyl)-N-($C_1$–$C_2$ hydroxyalkyl) glucamine sulfates, preferably those in which the $C_8$–$C_{17}$ acyl group is derived from coconut or palm kernel oil. These materials can be prepared by the method disclosed in U.S. Pat. No. 2,717,894, issued Sep. 13, 1955 to Schwartz.

The counterion for the anionic surfactant component may be any cation capable of forming a water soluble salt. Representative counterions include, for example, $Na^+$, $K^+$divalent cations such as $Mg^{++}$ and $Ca^{++}$, $Al3^+$, ammonium and substituted ammonium such as alkanolammonium. Suitable alkanolammonium ions include those formed from mono-, di-, and triethanolamines. Preferred counterions are divalent cations, such as, for example, magnesium and calcium. Magnesium is a particularly preferred counterion for the anionic surfactant.

Foam Stabilizing Auxiliary Surfactant

The detergent compositions of the present invention also comprise from about 1% to about 20%, preferably from about 2% (more preferably 3 to 5%) to about 20% by weight of a foam stabilizing surfactant selected from the group consisting of amides, amine oxides, betaines, sultaines and $C_8$–$C_{18}$ fatty alcohols.

Amine oxides useful in the present invention include longchain alkyl amine oxides, i.e., those compounds having the formula

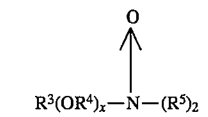

wherein $R^3$ is selected from an alkyl, hydroxyalkyl, acylamidopropyl and alkyl phenyl group, or mixtures thereof, containing from 8 to 26 carbon atoms, preferably 8 to 16 carbon atoms; $R^4$ is an alkylene or hydroxyalkylene group containing from 2 to 3 carbon atoms, preferably 2 carbon atoms, or mixtures thereof; x is from 0 to 3, preferably 0; and each $R^5$ is an alkyl or hydroxyalkyl group containing from 1 to 3, preferably from 1 to 2 carbon atoms, or a polyethylene oxide group containing from 1 to 3, preferably 1, ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxyethyl amine oxides. Examples of such materials include dimethyloctylamine oxide, diethyldecylamine oxide, bis-(2-hydroxyethyl)dodecylamine oxide, dimethyldodecylamine oxide, dodecylamidopropyl dimethylamine oxide and dimethyl-2-hydroxyoctadecylamine oxide. Preferred are $C_{10}$–$C_{18}$ alkyl dimethylamine oxide, and $C_{10}$–$C_{18}$ acylamido alkyl dimethylamine oxide.

The betaines useful in the present invention are those compounds having the formula $R(R^1)_2N^+R^2COO^-$ wherein R is a $C_6$–$C_{18}$ hydrocarbyl group, preferably $C_{10}$–$C_{16}$ alkyl group, each $R^1$ is typically $C_1$–$C_3$, alkyl, preferably methyl, and $R^2$ is a $C_1$–$C_5$ hydrocarbyl group, preferably a $C_1$–$C_5$ alkylene group, more preferably a $C_1$–$C_2$ alkylene group. Examples of suitable betaines include coconut acylamidopropyldimethyl betaine; hexadecyl dimethyl betaine; $C_{12}$–$C_{14}$ acylamidopropylbetaine; $C_8$–$C_{14}$ acylamidohexyldiethyl betaine; 4-[$C_{14}$–$C_{16}$ acylmethylamidodiethylammonio]-1-carboxybutane; $C_{16}$–$C_{18}$ acylamidodimethylbetaine; $C_{12}$–$C_{16}$ acylamidopentanediethylbetaine; $C_{12}$–$C_{16}$ acylmethyl-amidodimethylbetaine. Preferred betaines are $C_{12}$–$C_{18}$ dimethylamoniohexanoate and the $C_{10}$–$C_{18}$ acylamidopropane (or ethane) dimethyl (or diethyl) betaines.

The sultaines useful in the present invention are those compounds having the formula $R(R^1)_2N^+R^2SO_3^{31}$ wherein R is a $C_6$–$C_{18}$ hydrocarbyl group, preferably a $C_{10}$–$C_{16}$ alkyl group, more preferably a $C_{12}$–$C_{13}$ alkyl group, each $R_1$ is typically $C_1$–$C_3$ alkyl, preferably methyl, and $R_2$ is a $C_1$–$C_6$ hydrocarbyl group, preferably a $C_1$–$C_3$ alkylene or, preferably, hydroxyalkylene group. Examples of suitable sultaine, $C_{12}$–$C_{14}$ dihydroxyethylammonio propane sulfonate, and $C_{16}$–$C_{18}$ dimethylammonio hexane sulfonate, with $C_{12}$–$C_{14}$ amido propyl ammonio-2-hydroxypropyl sultaine being preferred.

The auxiliary foam stabilizing surfactant may also be a fatty acid amide surfactant. Preferred amides are $C_8$–$C_{20}$ alkanol amides, monoethanolamides, diethanolamides, and isopropanolamides. A particularly preferred amide is a mixture of myristic monoethanolamide and lauric monoethanolamide. This preferred amide is sold by Stepan Company, Northfield, Ill. as Ninol LMP.

Divalent Cation

The technique of incorporating the divalent cation, preferably magnesium, into the compositions of the present invention is not thought to be critical and can be accomplished in a number of ways.

Thus, individual anionic surfactants can be made as aqueous solutions of alkali metal or ammonium salts which are then mixed together with a water-soluble divalent salt, such as, for example, the chloride or sulfate of calcium or magnesium. Optional minor ingredients may then be added before pH and viscosity are adjusted. This method has the advantage of utilizing conventional techniques and equipment but does result in the introduction of additional chloride or sulfate ions which can increase the chill point temperature (the temperature at which inorganic salts precipitate as crystals in the liquid), also known as the cloud-point.

If the anionic surfactants are in the acid form, then the divalent cation can be added by neutralization of the acid with a divalent oxide, such as a magnesium oxide or magnesium hydroxide slurry in water. This technique avoids the addition of chloride and sulfate ions, therefore eliminating or reducing the corrosiveness of the composition. The neutralized surfactant salts are then added to the final mixing tank and any optional ingredients are added before adjusting the pH.

A third technique, and the most preferred, is to add one or more of the anionic surfactants as a salt or salts of the divalent cation.

Liquid Carrier

In a preferred embodiment, the detergent compositions of the present invention are liquid detergent compositions. These preferred liquid detergent compositions comprise from about 95% to about 35% by weight, preferably from about 90% to about 50% by weight, most preferably from about 80% to about 60% by weight of a liquid carrier. Although the liquid carrier may consist of water as the sole component, typical liquid carriers comprise a mixture of water and a $C_1$–$C_4$ monohydric alcohol (e.g., ethanol, propanol, isopropanol, butanol, and mixtures thereof), with ethanol being the preferred alcohol. Preferred amounts of ethanol are from about 1 to 10% by weight of the composition.

Composition pH

The liquid detergent compositions hereof will preferably be formulated such that during use in aqueous cleaning operations the wash water will have a pH of between about 6.0 and about 7.0, more preferably between about 6.5 and about 8.0. Liquid product formulations preferably have a pH in the range of from about 5.0 to about 10.5, preferably from about 6.0 to about 9.0, most preferably from about 6.0 to about 7.0. Techniques for controlling pH at recommended usage levels include the use of buffers, alkali, acids, etc., and are well known to those skilled in the art.

Thickening Agent

The detergent compositions of the present invention may also be in the form of a gel. Such compositions are typically formulated in the same manner as liquid detergent compositions, except they contain an additional thickening agent.

Any material or materials which can be admixed with the aqueous liquid to provide shear-thinning compositions having sufficient yield values can be used in the compositions of this invention. Materials such as colloidal silica, particulate polymers, such as polystyrene and oxidized polystyrene, combinations of certain surfactants, and water-soluble polymers such as polyacrylate are known to provide yield values.

A preferred thickening agent useful in the compositions of the present invention is a high molecular weight polycarboxylate polymer thickener. By "high molecular weight" it is meant from about 500,000 to about 5,000,000, preferably from about 750,000 to about 4,000,000.

The polycarboxylate polymer may be a carboxyvinyl polymer. Such compounds are disclosed in U.S. Pat. No. 2,798,053, which is incorporated herein by reference. Methods for making carboxyvinyl polymers are also disclosed in Brown, and are also incorporated herein by reference.

A carboxyvinyl polymer is an interpolymer of a monomeric mixture comprising a monomeric olefinically unsaturated carboxylic acid, and from about 0.1% to about 10% by weight of the total monomers of a polyether of a polyhydric alcohol, which polyhydric alcohol contains at least four carbon atoms to which are attached at least three hydroxyl groups, the polyether containing more than one alkenyl group per molecule. Other monoolefinic monomeric materials may be present in the monomeric mixture if desired, even in predominant proportion. Carboxyvinyl polymers are substantially insoluble in liquid, volatile organic hydrocarbons and are dimensionally stable on exposure to air.

Preferred polyhydric alcohols used to produce carboxyvinyl polymers include polyols selected from the class consisting of oligosaccharides, reduced derivatives thereof in which the carbonyl group is converted to an alcohol group, and pentaerythritol; more preferred are oligosaccharides, most preferred is sucrose. It is preferred that the hydroxyl groups of the polyol which are modified be etherified with allyl groups, the polyol having at least two allyl ether groups per polyol molecule. When the polyol is sucrose it is preferred that the sucrose have at least above five allyl ether groups per sucrose molecule. It is preferred that the polyether of the polyol comprise from about 0.1% to about 4% of the total monomers, more preferably from about 0.2% to about 2.5%.

Preferred monomeric olefinically unsaturated carboxylic acids for use in producing the carboxyvinyl polymers used herein include monomeric, polymerizable, alpha-beta monoolefinically unsaturated lower aliphatic carboxylic acids; most preferred is acrylic acid.

Carboxyvinyl polymers useful in formulations of the present invention have a molecular weight of at least about 750,000. Preferred are highly cross-linked carboxyvinyl polymers having a molecular weight of at least about 1,250,000. Also preferred are carboxyvinyl polymers having a molecular weight of at least about 3,000,000, which may be less highly cross-linked.

Various carboxyvinyl polymers are commercially available from B.F. Goodrich Company, New York, N.Y., under the trade name Carbopol. Carboxyvinyl polymers useful in formulations of the present invention include Carbopol 910 having a molecular weight of about 750,000; preferred is Carbopol 941 having a molecular weight of about 1,250,000, and more preferred are Carbopols 934 and 940 having molecular weights of about 3,000,000 and 4,000,000, respectively.

Carbopol 934 is a very slightly cross-linked carboxyvinyl polymer having a molecular weight of about 3,000,000. It has been described as a high molecular weight polyacrylic acid cross-linked with about 1% of polyallyl sucrose having an average of about 5.8 allyl groups for each molecule of sucrose.

Additional polycarboxylate polymers useful in the present invention are Sokolan PHC-25$^R$, a polyacrylic acid available from BASF Corp., and Gantrez® a poly(methyl vinyl ether/maleic acid) interpolymer available from GAF Corp.

Preferred polycarboxylate polymers of the present invention are non-linear, water-dispersible, polyacrylic acid cross-linked with a polyalkenyl polyether and having a molecular weight of from about 750,000 to about 4,000,000.

Highly preferred examples of these polycarboxylate polymer thickeners are the Carbopol 600 series resins available from B.F. Goodrich. Especially preferred are Carbopol 616 and 617. It is believed that these resins are more highly cross-linked than the 900 series resins and have molecular weights between about 1,000,000 and 4,000,000. Mixtures of polycarboxylate polymers as herein described may also be used in the present invention. Particularly preferred is a mixture of Carbopol 616 and 617 series resins.

The polycarboxylate polymer thickener is utilized preferably with essentially no clay thickening agents. In fact, it has been found that it the polycarboxylate polymers of the present invention are utilized with clay in the composition of the present invention, a less desirable product, in terms of phase instability, results. In other words, the polycarboxylate polymer is preferably used instead of clay as a thickening/stabilizing agent in the present compositions.

Without intending to be bound by a particular theory, it is believed that the long chain molecules of the polycarboxylate polymer thickener help suspend solids in the thickened detergent compositions of the present invention and help keep the matrix expanded. The polymeric material is also less sensitive than clay thickeners to destruction due to repeated shearing, such as occurs when the compositions is vigorously mixed.

If the polycarboxylate polymer is used as a thickening agent in the compositions of the present invention, it is typically present at a level of from about 0.1% to about 10%, preferably from about 0.2% to about 2% by weight.

Other thickening agents suitable are cellulose and various cellulose derivatives, various methocels and natrosols, xanthan gum, and mixtures thereof.

Optional Components

Other anionic surfactants useful for detersive purposes can also be included in the compositions hereof. Exemplary, nonlimiting useful anionics include salts (e.g., sodium, potassium, ammonium, and substituted ammonium salts such as mono-, di- and triethanolamine salts) of soap, sulfonated polycarboxylic acids prepared by sulfonation of the pyrolyzed product of alkaline earth metal citrates, e.g., as described in British patent specification No. 1,082,179, $C_8$–$C_{22}$ alkylsulfates, $C_8$–$C_{24}$ alkylpolyglycolethersulfates (containing up to 10 moles of ethylene oxide); alkyl glycerol sulfonates, fatty acyl glycerol sulfonates, fatty acyl glycerol sulfates, alkyl phenol ethylene oxide ether sulfates, alkyl phosphates, isethionates such as the acyl isethionates, acyl taurates, fatty acid amides, alkyl succinates and sulfosuccinates, acyl sarcosinates, sulfates of alkyl polysaccharides such as the sulfates of alkylpolyglucoside (the nonionic nonsulfated compounds having already been described herein), alkyl ether carbonates, alkyl ethoxy carboxylates, fatty acids esterified with isethionic acid and neutralized with sodium hydroxide, and fatty acids amides of methyl tauride. Further examples are described in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23 (herein incorporated by reference).

Nonionic Detergent Surfactants

Suitable nonionic detergent surfactants are generally disclosed in U.S. Pat. No. 3,929,678, Laughlin et al., issued Dec. 30, 1975, at column 13, line 14 through column 16, line 6, incorporated herein by reference. Exemplary, non-limiting classes of useful nonionic surfactants are listed below.

1. The polyethylene, polypropylene, and polybutylene oxide condensates of alkyl phenols. In general, the polyethylene oxide condensates are preferred. These compounds include the condensation products of alkyl phenols having an alkyl group containing from 6 to 12 carbon atoms in either a straight-or branched-chain configuration with the alkylene oxide. In a preferred embodiment, the ethylene oxide is present in an amount equal to from about 5 to about 25 moles of ethylene oxide per mole of alkyl phenol.

Commercially available nonionic surfactants of this type include Igepal™ CO-630, marketed by the GAF Corporation; and Triton™ X-45, X-114, X-100, and X-102, all marketed by the Rohm & Haas Company.

2. The condensation products of aliphatic alcohols with from about 1 to about 25 moles of ethylene oxide. The alkyl chain of the aliphatic alcohol can either be straight or branched, primary or secondary, and generally contains from 8 to 22 carbon atoms. Particularly preferred are the condensation products of alcohols having an alkyl group containing from about 10 to about 20 carbon atoms with from about 2 to about 10 moles of ethylene oxide per mole of alcohol. Examples of commercially available nonionic surfactants of this type include Tergitol™ 15-S-9 (the condensation product of $C_{11}$–$C_{15}$ linear alcohol with 9 moles ethylene oxide), Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45-9 (the condensation product of $C_{14}$–$C_{15}$ linear alcohol with 9 moles of ethylene oxide), Neodol™ 23-6.5 (the condensation product of $C_{12}$–$C_{13}$ linear alcohol with 6.5 moles of ethylene oxide), Neodol™ 45-7 (the condensation product of $C_{14}$–$C_{15}$ linear alcohol with 7 moles of ethylene oxide), Neodol™ 45-4 (the condensation product of $C_{14}$–$C_{15}$ linear alcohol with 4 moles of ethylene oxide), marketed by Shell Chemical Company, and Kyro™ EOB (the condensation product $C_{13}$–$C_{15}$ alcohol with 9 moles ethylene oxide), marketed by The Procter & Gamble Company.

3. The condensation products of ethylene oxide with a hydrophobic base formed by the condensation of propylene oxide with propylene glycol. The hydrophobic portion of these compounds preferably has a molecular weight of from about 1500 to about 1800 and exhibits water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially-available Pluronic™ surfactants, marketed by BASF.

4. The condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of popyoxyethylene and has a molecular weight of from about 5,000 to about 11,000. examples of this type of nonionic surfactant include certain of the commercially available Tetronic™ compounds, marketed by BASF.

5. Semi-polar nonionic surfactants are a special category of nonionic surfactants which include water-solube amine oxides containing one alkyl moiety of from 10 to 18 carbon atoms and 2 moieties selected from the group consisting of alkyl groups and hydroxyalkyl groups containing from 1 to 3 carbon atoms; and water-soluble sulfoxides containing one alkyl moiety of from 10 to 18 carbon atoms and a moiety selected from the group consisting of alkyl and hydroxlkyl moieties of from 1 to 3 carbon atoms.

Semi-polar nonionic detergent surfactants include the amine oxide surfactants. These amine oxide surfactants in particular include $C_{10}$–$C_{18}$ alkyl dimethyl amine oxides and $C_8$–$C_{12}$ alkoxy ethyl dihydroxy ethyl amine oxides.

6. Alkylpolysaccharides disclosed in U.S. Pat. No. 4,565,647, Llenado, issued Jan. 21, 1986, having a hydrophobic group containing from about 6 to about 30 carbon atoms, preferably from about 10 to about 16 carbon atoms and a polysaccharide, e.g., a polyglucoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

Optionally, and less desirably, there can be a polyalkyleneoxide chain joining the hydrophobic moiety and the polysaccharide moiety. The preferred alkyleneoxide is ethylene oxide. Typical hydrophobic groups include alkyl groups, either saturated or unsaturated, branched or unbranched containing from 8 to 18, preferably from 12 to 14 carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolethoxdy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominately the 2-position.

Optional Surfactants

Ampholytic surfactants may also be incorporated into the detergent compositions hereof. These surfactants can be broadly described as aliphatic derivatives of secondary or tertiary amines, or aliphatic derivatives of heterocyclic secondary and tertiary amines in which the aliphatic radical can be straight-branched chains. One of the aliphatic substituents contains at least 8 carbon atoms, typically from 8 to 18 carbon atoms, and at least one contains an anionic water-solubilizing group, e.g., carboxy, sulfonate, sulfate. See U.S. Pat. No. 3,929,678 to Laughlin et al., issued Dec. 30, 1975, at column 19, lines 18–35 (herein incorporated by reference) for examples of useful ampholytic surfactants.

Zwitterionic surfactants may also be incorporated into the detergent compositions hereof. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 to Laughlin et al., issued Dec. 30, 1975, at column 19, line 38 through column 22, line 48 (herein incorporated by reference) for examples of useful zwitterionic surfactants. Such ampholytic and zwitterionic surfactants are generally used in combination with one or more anionic and/or nonionic surfactants.

Preferred additional surfactants are anionic and nonionic surfactants. Preferred nonionic surfactants include polyethylene, polypropylene and polybutylene oxide condensates of alkyl phenols; the alkyl ethoxylate condensation products of aliphatic alcohols with ethylene oxide; the condensation products of ethylene oxide with a hydrophobic base formed by the condensation of propylene oxide with propylene glycol; the condensation product of ethylene oxide with the product resulting from the reaction of propylene oxide and ethylenediamine; alklpolysaccharides, more preferably alkylpolysaccharides having a hydrophobic group containing from about 6 to about 30 carbon atoms and a polysaccharide group containing from about 1.3 to about 10 saccharide units; fatty acid amides; and mixtures thereof.

If included in the compositions of the present invention, these optional additional surfactants are typically present at a concentration of from about 1.0% to about 15%, preferably from about 2% to about 10% by weight.

Other optional ingredients include detergency builders, either of the organic or inorganic type, although such builders in general are not preferred for use in the composition of the present invention. Examples of water-soluble inorganic builders which can be used, either alone or in admixture with themselves or with organic alkaline sequentrant builder salts, are glycine, alkyl and alkenyl succinates, alkali metal carbonates, alkali metal bicarbonates, phosphates, polyphosphates, and silicates. Specific examples of such salts are sodium tripolyphosphate, sodium carbonate, potassium carbonate, sodium bicarbonate, potassium bicarbonate, sodium pyrophosphate, potassium pyrophosphate. Examples of organic builder salts which can be used alone, or in admixture with each other, or with the preceding inorganic alkaline builder salts, are alkali metal polycarboxylates, examples of which include but are not limited to, water-soluble citrates such as sodium and potassium citrate, sodium and potassium tartrate, sodium and potassium ethylenediaminetetracetate, sodium and potassium N(2-hydroxyethyl)-nitrilo triacetates, sodium and potassium N-(2-hydroxyethyl)-nitrilo diacetates, sodium and potassium oxydisuccinates, and sodium and potassium tartrate mono- and di-succinates, such as those described in U.S. Pat. No. 4,663,071 (Bush et al., issued May 5, 1987), the disclosure of which is incorporated herein. Other organic detergency builders, such as water-soluble phosphonates, can be used in the compositions of the present invention. However, detergency builders in general have limited value when the compositions of the present invention are in the form of light-duty liquid dishwashing detergent compositions. If included in the compositions of the present invention, these optional builders are typically present at a concentration of from about 1.0% to about 10%, preferably from about 2% to about 5% by weight.

Other desirable ingredients include diluents, solvents, dyes, perfumes and hydrotropes. Diluents can be inorganic salts, such as sodium and potassium sulfate, ammonium chloride, sodium and potassium chloride, sodium bicarbonate, etc. Diluents useful in the compositions of the present invention are typically present at levels of from about 1% to about 10%, preferably from about 2% to about 5% by weight.

Solvents useful herein include water and lower molecular weight alcohols, such as ethyl alcohol, isopropyl alcohol, etc. Solvents useful in the compositions of the present invention are typically present at levels of from about 1% to about 60%, preferably from about 5% to about 50% by weight.

Traditional hydrotropes such as sodium and potassium toluene sulfonate, sodium and potassium xylene sulfonate, sodium and potassium cumene sulfonate, trisodium and tripotassium sulfosuccinate, and related compounds (as disclosed in U.S. Pat. No. 3,915,903, the disclosure of which is incorporated herein) can be utilized in the compositions. Although such hydrotropes may be used, they are not normally needed in the inventive compositions. Without being bound by any particular theory, it is presently believed that the hydrotropic surfactants, i.e., the alpha-sulfonated alkyl esters, possess dual functionality in that they act as a surfactant and also function as a hydrotrope. Preferred compositions do not include traditional hydrotropes since they do not contribute towards the cleaning and grease-cutting capabilities of the compositions. Thus, in preferred compositions, the sole hydrotrope is the alkyl ester sulfonate. Such compositions are substantially free from traditional hydrotropes based on (1) aromatic sulfonates and (2) sulfonated carboxylic acids.

The cleaning compositions may also contain one or more polyhydroxy fatty acid amides having the structural formula:

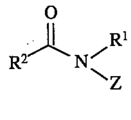

wherein: $R^1$ is H, $C_1$–$C_4$ hydrocarbyl, 2-hydroxy ethyl, 2-hydroxy propyl, or a mixture thereof, preferably $C_1$–$C_4$ alkyl, more preferably $C_1$ or $C_2$ alkyl, most preferably $C_1$ alkyl (i.e., methyl); and $R^2$ is a $C_5$–$C_{31}$ hydrocarbyl, preferably straight-chain $C_7$–$C_{19}$ alkyl or alkenyl, more preferably straight-chain $C_9C_{17}$ alkyl or alkenyl, most preferably straight-chain $C_{11}$–$C_{17}$ alkyl or alkenyl, or mixture thereof; and Z is a polyhydroxyhydrocarbyl having a linear hydrocarbyl chain with at least 3 hydroxyls directly connected to the chain, or an alkylated derivative (preferably ethoxylated or propoxylated) thereof. Z preferably will be derived from a reducing sugar in a reductive amination reaction; more preferably Z is a glycityl. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of of $—CH_2—(CHOH)_n—CH_2OH$, $—CH(CH_2OH)—(CHOH)_{a-1}CH_2OH$, $—CH_2—(CHOH)_2(CHOR')—CH_2OH$, where n is an integer from 3 to 5, inclusive, and $R^1$ is H or a cyclic or aliphatic monosaccharide, and alkoxylated derivatives thereof. Most preferred are glycityls wherein n is 4, particularly $—CH_2—(CHOH)_4—CH_2OH$.

$R^1$ can be, for example, N-methyl, N-ethyl, N-propyl, N-isopropyl, N-butyl, N-2-hydroxy ethyl, or N-2-hydroxy propyl.

$R^2$-CO-N< can be, for example, cocamide, stearamide, oleamide, lauramide, myristamide, capricamide, palmitamide, tallowamide, etc.

Z can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

Optional ingredients useful when the compositions of the present invention are used in liquid dishwashing detergent applications include drainage promoting ethoxylated nonionic surfactants of the type disclosed in U.S. Pat. No. 4,316,824, issued to Pancheri on Feb. 23, 1982, the disclosure of which is incorporated herein.

In the method aspect of this invention, soiled dishes are contacted with an effective amount, typically from about 0.5 ml to about 20 ml. (per 25 dishes being treated), preferably from about 3 ml. to about 10 ml., of the composition of the present invention. The actual amount of liquid detergent composition used will be based on the judgment of user, and will typically depend upon factors such as the particular product formulation of the composition, including the concentration of active ingredient in the composition, the number of soiled dishes to be cleaned, the degree of soiling on the dishes, and the like. The particular product formulation, in turn, will depend upon a number of factors, such as the intended market (i.e., U.S., Europe, Japan, etc.) for the composition product. The following are examples of typical methods in which the detergent compositions of the present invention may be used to clean dishes. These examples are for illustrative purposes and are not intended to be limiting.

In a typical U.S. application, from about 3 ml to about 15 ml, preferably from about 5 ml to about 10 ml of a liquid detergent composition is combined with from about 1,000 ml to about 10,000 ml, more typically from about 3,000 ml to about 5,000 ml of water in a sink having a volumetric capacity in the range of from about 5,000 ml to about 20,000 ml, more typically from about 10,000 ml to about 15,000 ml. The detergent composition has a surfactant mixture concentration of from about 21% to about 44% by weight, preferably from about 25% to about 40% by weight. The soiled dishes are immersed in the sink containing the detergent composition and water, where they are cleaned by contacting the soiled surface of the dish with a cloth, sponge, or similar article. The cloth, sponge, or similar article may be immersed in the detergent composition and water mixture prior to being contacted with the dish surface, and is typically contacted with the dish surface for a period of time ranging from about 1 to about 10 seconds, although the actual time will vary with each application and user. The contacting of the cloth, sponge, or similar article to the dish surface is preferably accompanied by a concurrent scrubbing of the dish surface.

In a typical European market application, from about 3 ml to about 15 ml, preferably from about 3 ml to about 10 ml of a liquid detergent composition is combined with from about 1,000 ml to about 10,000 ml, more typically from about 3,000 ml to about 5,000 ml of water in a sink having a volumetric capacity in the range of from about 5,000 ml to about 20,000 ml, more typically from about 10,000 ml to about 15,000 ml. The detergent composition has a surfactant mixture concentration of from about 21% to about 44% by weight, preferably from about 25% to about 35% by weight. The soiled dishes are immersed in the sink containing the detergent composition and water, where they are cleaned by contacting the soiled surface of the dish with a cloth, sponge, or similar article. The cloth, sponge, or similar article may be immersed in the detergent composition and water mixture prior to being contacted with the dish surface, and is typically contacted with the dish surface for a period of time ranging from about 1 to about 10 seconds, although the actual time will vary with each application and user. The contacting of the cloth, sponge, or similar article to the dish surface is preferably accompanied by a concurrent scrubbing of the dish surface.

Depending on the desires of the formulator, the compositions herein can contain more or less of various suds control agents. Typically, for dishwashing, high sudsing is desirable so no suds control agent will be used. For fabric laundering in top-loading washing machines some control of suds may be desirable, and for front-loaders some considerable degree of suds control may be preferred. A wide variety of suds control agents are known in the art and can be routinely selected for use herein. Indeed, the selection of suds control agent, or mixtures of suds control agents, for any specific detergent composition will depend not only on the presence and amount of polyhydroxy fatty acid amide used therein, but also on the other surfactants present in the formulation. However, it appears that, for use with polyhydroxy fatty acid amides, silicone-based suds control agents of various types are more efficient (i.e. lower levels can be used) than various other types of suds control agents. The silicone suds control agents available as AE, X2-3419, Q2-3302 and DC-544 (Dow Corning) are particularly useful.

The formulator of fabric laundering compositions which can advantageously contain soil release agent has a wide variety of known materials to choose from (see, for example, U.S. Pat. No. 3,962,152; 4,116,885; 4,238,531; 4,702,857; and 4,877,896). Additional soil release materials useful herein include the nonionic oligomeric esterification product of a reation mixture comprising a source of $C_1$–$C_4$ alkoxy-terminated polyethoxy units (e.g., $CH_3[OCH_2CH_2]_{16}OH$), a source of terephthaloyl units (e.g., dimethyl terephthalate); a source of poly(oxyethylene)oxy units (e.g., polyethylene glycol 1500); a source of oxyiso-propyleneoxy units (e.g., 1,2-propylene glycol); and a source of oxyethyleneoxy units (e.g., 1,2-propylene glycol); and a source of oxyethyleneoxy units (e.g., ethylene glycol) especially wherein the mole ratio of oxyethyleneoxy units:oxyiso-propyleneoxy units is at least about 0.5:1.

Another preferred type of soil release agent useful herein is of the general anionic type described in U.S. Pat. No. 4,877,896, but with the condition that such agents be substantially free of monomers of the HOROH type wherein R is propylene or higher alkyl. Thus, the soil release agents of U.S. Pat. No. 4,877,896, but with the condition that such agents be substantially free of monomers of the HOROH type wherein R is propylene or higher alkyl. Thus, the soil release agents of U.S. Pat. No. 4,877,896 can comprise, for example, the reaction product of dimethyl terephthalate, ethylene glycol, 1,2-propylene glycol and 3-sodiosulfobenzoic acid, whereas these additional soil release agents can comprise, for example, the reaction product of dimethyl terephthalate, ethylene glycol, 5-sodiosulfoisophthalate and 3-sodiosulfobenzoic acid. Such agents are preferred for use in granular laundry detergents.

The formulator may also determine that it is advantageous to include a non-perborate bleach, especially in heavy-duty granular laundry detergents. A variety of peroxygen bleaches are available, commercially, and can be used herein, but, of these, percarbonate is convenient and economical. Thus, the compositions herein can contain a solid percarbonate bleach, normally in the form of the sodium salt, incorporated at a level of from 3% to 20% by weight, more perferably from 5% to 18% by weight and most preferably from 2% to 15% by weight of the composition.

Sodium percarbonate is an addition compound having a formula corresponding to $2Na_{22}CO_2.3H_2O_2$, and is available commercially as a crystalline solid. Most commercially available material includes a low level of a heavy metal sequestrant such as EDTA, 1-hydroxyethylidene 1,1-diphosphonic acid (HEDP) or an aminophosphonate, that is incorporated during the manufacturing process. For use herein, the percarbonate can be incorporated into detergent compositions without additional protection, but preferred embodiments of the invention utilize a coated form of the material. Although a variety of coatings can be used, the most economical is sodium silicate of $SiO_o$:$Na_2O$ ratio from 1.6:1 to 2.8:1, preferably 2.0:1, applied as an aqueous solution and dried to give a level of from 2% to 10% (normally from 3% to 5%), of silicate solids by weight of the percarbonate.

Magnesium silicate can also be used and a chelant such as one of those mentioned above can also be included in the coating.

The particle size range of the crystalline percarbonate is from 350 micrometers to 450 micrometers with a mean of approximately 400 micrometers. When coated, the crystals have a size in the range from 400 to 600 micrometers.

While heavy metals present in the sodium carbonate used to manufacture the percarbonate can be controlled by the inclusion of sequestrants in the reaction mixture, the percarbonate still requires protection from heavy metals present as impurities in other ingredients of the product. It has been found that the total level of iron, copper and manganese ions in the product should not exceed 25 ppm and preferably should be less than 20 ppm in order to avoid an unacceptably adverse effect on percarbonate stability.

One skilled in the art will recognize that modifications may be made in the present invention without deviating from the spirit or scope of the invention. The invention is illustrated further by the following examples which are not to be construed as limiting the invention or scope of the specific procedures described herein.

EXAMPLE 1

Mini-Plate Test

The capability of various formulations for cleaning and degreasing was determined by the Mini-Plate Test, as follows:

Preparation of Soil Material

1. Melt shortening (Crisco, approx. 100 g) in a beaker at 160° F.

2. Add a small amount (not much needed for deep color) of red dye to melted Crisco and stir until dissolved.

3. Calibrate syringe to deliver 0.36 g of Crisco soil on each plate.

4. Apply 0.36 g of Crisco oil to each of the larger watchglasses.

5. When all of the larger watchglasses have been soiled, recalibrate syringe to deliver 0.12 g of Crisco soil to each plate.

6. Apply 0.12 g of Crisco soil to each of the smaller watchglasses.

7. Allow soiled watchglasses to harden at room temperature overnight before using.

8. Soiled watchglasses should always be stored at room temperature (can be stored indefinitely).

Procedure for Analyzing Test Formulations

1. Test resolution is made by diluting 6 ml of product to be tested to 250 ml with D.I. water in volumetric flask.

2. A 25 ml aliquot of this solution is then added to the Pyrex dish and the volume of solution raised to 400 ml by adding the necessary amount of tap water, which has been heated to about 130°–135° F. Thus, the test is run at about 0.15% product concentration.

3. The solution in the dish is then agitated with the paintbrush to generate foam, until the temperature of the solution has dropped to 120° F.

4. At this point, the large watchglasses (which represent three plates each) are washed, one every 45 seconds, by removing a thin layer of soil at a time from the surface of the plate with the paintbrush, then agitating the paintbrush in the solution to remove the adhering soil (which consequently breaks down the foam).

5. As the endpoint (the point at which further agitation of the solution fails to produce additional foam on the surface) draws near, it is then advisable to switch to washing the smaller watchglasses (representing one plate each), one every 15 seconds, until the foam completely dies.

The endpoint of the test is the number of mini-plates washed before foam disappears.

The compositions in the following examples were all formulated on a weight percent basis.

EXAMPLE 2

These compositions may be prepared according to the process set forth below:

A surfactant paste is initially formed by combining any desired surfactants with water and optionally alcohol. Ideally the surfactant paste should be pumpable at room or elevated temperatures. Separately, in a large mixing vessel having a propeller mixer, three-quarters of the water of the formulated product, one-half of the alcohol of the formulated product, and any required hydrotropes (e.g., xylene, cumene, toluene sulfonates) are combined with mixing to give a clear solution. If the divalent cation, e.g., magnesium, is not added to the composition as the divalent salt of an anionic surfactant, the divalent cation may be added next, followed by the surfactant paste, to form a mixture.

The divalent cation may be added directly to the mixing vessel as, for example, magnesium chloride, magnesium sulfate, or as magnesium oxide or hydroxide powder. The magnesium oxide or hydroxide powder is added to the acid form of the surfactant salts (e.g., alkyl benzene sulfonates, alkyl sulfates, alkyl ethoxylated sulfates, methyl ester sulfonates, etc.) in the surfactant paste. When magnesium is added as an oxide or hydroxide powder, a less than stoichiometrially required amount is added with mixing to ensure complete dissolution. The pH of the magnesium-containing surfactant paste is then adjusted by using an additional amount of an $MgO$, $Mg(OH)_2$, $NaOH$ or $KOH$ solution.

The mixture is mixed until a homogenous, clear solution product is obtained. Additional water, alcohol, and any desired additional hydrotropes (added as a solution) may then be added to trim the solution product viscosity to the desired level, normally from 50–1000 Cps, and ideally between 200 and 700 cps, as measured by a Brookfield viscometer at 70° F. The pH of the solution product is then adjusted with either citric acid or NaOH to a level of 6.0 to 7.0 for formulas containing ammonium ions, and 7.5±1.5 for formulas substantially free from ammonium ions.

Perfume, dye and other ingredients, e.g., opacifying agents such as Lytron and ethylene glycol disterate, are added as the last step. Lytron can be added directly as a dispersion with mixing. Ethylene glycol distearate must be added in a molten state with rapid mixing to form the desired pearlescent crystals.

Specifically, Formula 3, shown in Table 1 below, was prepared as follows:

To a suitable vessel equipped with heating, cooling and mixing means was added 11.4 g of water (deionized) and 48.0 g of 50% aqueous magnesium linear alkyl benzene sulfonate. After these ingredients were mixed, 6.6 g of 60% aqueous ammonium lauryl ether sulfate (Steol CA-460) and 24 g of sodium alpha-sulfonated methyl ester of $C_{12}$–$C_{14}$ fatty acid (average carbon chain length: 13.6, 36.6% aqueous) were added and mixed until the mixture was uniform. The mixture was heated to 140°–145° F. at which time 5.0 g of lauric myristic monoethanol amide (Ninol LMP) was added and mixed until the amide had melted. The composition was then cooled to about 90° F. 3A ethanol added to the mixture, and the pH adjusted to 6.0 to 7.0 with MgO or triethanolamine. The composition was subsequently evaluated.

The degree of grease removal obtained from the detergent mixture is greater than that achieved by either of the individual detergents alone when used under normal conditions.

EXAMPLE 3

Formulations 1–3 were prepared essentially according to the procedure set forth in Example 2.

| | 1 % | 2 % | 3 % |
|---|---|---|---|
| MgLAS[1] | 29.94 | — | — |
| Steol CA-460 (60%)[2] | — | 29.94 | — |
| NaMC-48[3] | — | — | 29.94 |
| Ninol LMP | 4.05 | 4.05 | 4.05 |
| SXS[4] | 3.0 | 3.0 | 3.0 |
| NaOH 50%[5] | — | 0.20 | 0.20 |
| Citric Acid | 0.025 | — | — |

-continued

| | 1 % | 2 % | 3 % |
|---|---|---|---|
| DI Water | Q.S to 100% | Q.S to 100% | Q.S to 100% |
| Ethanol 3A | 5.0 | — | 5.0 |
| % Surfactant | 33.99 | 33.99 | 33.99 |
| Mini Plates Washed | 39 | 36 | 33 |
| Appearance | Clear | Clear | Clear |
| pH (adjusted) | 6.8 | 6.8 | 6.7 |
| pH (initial) | 8.2 | 4.80 | 4.3 |
| Appearance (0.15 g in water) | Turbid | Clear | Clear |

[1]magnesium salt of linear alkyl benzene sulfonate having an average of 11.5 carbon atoms in the alkyl portion (LAS).
[2]sodium salt of ethoxylated lauryl sulfate having an average of 3 moles of ethylene oxide (AES) containing about 15% ethanol.
[3]sodium salt of alpha-sulfonated methyl ester of fatty acids having an average of 12 to 14 carbon atoms (MES) where the average carbon chain length is 13.6, ratio of mono-sodium salt to di-sodium salt is about 9:1.
[4]lauric myristic monoethanolamide.
[5]sodium xylene sulfonate

EXAMPLE 4

Formulations 4–7 were prepared essentially according to the procedure set forth in Example 2.

| | 4 | 4b | 4c | 4d | 5 | 6 | 7 |
|---|---|---|---|---|---|---|---|
| Ingredient, % Active | | | | | | | |
| MgLAS | 19.44 | 19.44 | 19.44 | 19.44 | — | — | — |
| NaLAS[1] | — | — | — | — | 19.44 | 19.44 | 17.00 |
| $NH_4AES$[2] | 3.22 | 3.22 | 3.22 | 3.22 | 3.22 | 3.22 | 13.00 |
| NaMES[3] | 7.12 | — | — | — | 7.12 | 7.12 | — |
| $NaC_{14}MES$[4] | — | 7.12 | — | — | — | — | — |
| $NaC_{16}$–$C_{18}MES$[5] | — | — | 7.12 | — | — | — | — |
| $NaC_{12}MES$[6] | — | — | — | 7.12 | — | — | — |
| LMMEA[7] | 4.05 | 4.05 | 4.05 | 4.05 | 4.05 | 4.05 | 4.00 |
| $MgSO_4.7H_2O$ | — | — | — | — | — | 3.00 | — |
| MgO | — | — | — | 0.05 | — | — | — |
| DI Water | Q.S. to 100% | Q.S. to 100% | Q.S. to 100% | Q.S. to 100% | Q.S. to 100% | Q.S. to 100% | Q.S. to 100% |
| Surfactant, % | 33.80 | 33.80 | 33.80 | 33.80 | 33.80 | 33.80 | 34.0 |
| Total Ethanol[8], % | 5.00 | 5.00 | 5.00 | 5.00 | 5.00 | 5.00 | — |
| Appearance @ 25 C. | Clear | Clear | Clear | Clear | Clear | Clear | Clear |
| Mini Plates Washed | 51 | 51 | 42 | 48 | 42 | 45 | 42 |

[1]sodium salt of linear alkyl benzene sulfonate (LAS) having an average alkyl portion of 11.5 carbon atoms.
[2]ammonium salt of AES (ethoxylated lauryl sulfate) having an average of 3 moles ethylene oxide.
[3]sodium salt of MES (alpha-sulfonated methyl ester of fatty acids having an average of 12–14 carbon atoms).
[4]sodium salt of sulfonated methyl ester of C14 fatty acid.
[5]sodium salt of sulfonated methyl ester of tallow ($C_{16}$–$C_{18}$) fatty acid.
[6]sodium salt of sulfonated methyl ester of $C_{12}$ fatty acid.
[7]lauric myristic monoethanolamide.
[8]includes ethanol contributed by $NH_4AES$.

EXAMPLE 5

Formulations 8–12 were prepared essentially according to the procedure set forth in Example 2.

| | 8 | 9 | 10 | 11 | 12 |
|---|---|---|---|---|---|
| NaLAS | — | — | — | — | 17.0 |
| MgLAS | 19.44 | 19.44 | 19.44 | 19.44 | — |
| $NH_4AES$ | 10.34 | 3.22 | 3.22 | — | 13.0 |
| NaMES | — | — | 7.12 | 10.34 | — |
| LMMEA | 4.05 | 4.05 | 4.05 | 4.05 | 4.0 |
| MgMES | — | 7.12 | — | — | — |
| MgO | — | 0.05 | 0.05 | 0.05 | — |
| DI Water | O.S. to 100% | Q.S. to 100% | Q.S. to 100% | Q.S. to 100% | Q.S. to 100% |

-continued

| | 8 | 9 | 10 | 11 | 12 |
|---|---|---|---|---|---|
| Surfactant, % | 33.8 | 33.8 | 33.8 | 33.8 | 34.0 |
| Total Ethanol, % | 5.00 | 5.00 | 5.00 | 5.00 | — |
| Appearance @ 25 C. | Hazy | Clear | Clear | Clear | Clear |
| Mini Plates Washed | 45 | 51 | 51 | 48 | 42 |

EXAMPLE 6

Formulations 13–17 were prepared essentially according to the procedure set forth in Example 2.

| Ingredient | 13 | 14 | 15 | 16 | 17 |
|---|---|---|---|---|---|
| MgLAS | 19.44 | — | — | 19.44 | — |
| NaLAS | — | 19.44 | 19.44 | — | 17.0 |
| $NH_4$AES | 3.22 | 3.22 | 3.22 | 3.22 | 13.0 |
| MgMES | 7.12 | 7.12 | — | — | — |
| NaMES | — | — | 7.12 | — | — |
| LMMEA | 4.05 | 4.05 | 4.05 | 4.05 | 4.0 |
| MgO | — | 0.05 | — | — | — |
| SXS | — | — | — | 7.12 | — |
| D.I. Water | Q.S. to 100% | Q.S. to 100% | Q.S. to 100% | Q.S. to 100% | Q.S. to 100% |
| Surfactant, % | 33.80 | 33.80 | 33.80 | 33.80 | 34.0 |
| Total Ethanol, % | 5.00 | 5.00 | 5.00 | — | — |
| Appearance @ 25 C. | Clear | Clear | Clear | Clear | Clear |
| Mini Plates Washed | 51 | 45 | 42 | 42 | 42 |

EXAMPLE 7

Formulations 18–23 were prepared essentially according to the procedure set forth in Example 2.

| | 18 | 19 | 20 | 21 | 22 | 23 |
|---|---|---|---|---|---|---|
| MgLAS | 19.44 | 19.44 | 19.44 | 19.44 | 19.44 | 19.44 |
| $NH_4$AES | 3.22 | 3.22 | 3.22 | 3.22 | 3.22 | 3.22 |
| NaMES | 7.12 | 7.12 | 7.12 | 7.12 | 7.12 | 7.12 |
| LMMEA | 4.05 | — | — | — | — | — |
| Lauryl Dimethyl Amine Oxide | — | 4.05 | — | — | — | — |
| Cocomido propyl betaine | — | — | 4.05 | — | — | — |
| NaLauryl sulfo acetate | — | — | — | 4.05 | — | — |
| Alkyl polyglycoside | — | — | — | — | 4.05 | — |
| 75:25 mixture of $C_{12}$ and $C_{14}$ N-methyl Glucamides | — | — | — | — | — | 4.05 |
| Ethanol | 5.0 | 5.0 | 5.0 | 5.0 | 5.0 | 5.0 |
| MgO | 0.05 | 0.05 | 0.05 | 0.05 | 0.05 | 0.05 |
| D.I. Water | Q.S to 100% | Q.S. to 100 | Q.S to 100% | Q.S. to 100 | Q.S to 100% | Q.S. to 100 |
| % Surfactant | 33.80 | 33.80 | 33.80 | 33.80 | 33.80 | 33.80 |
| Performance | 51 | 42 | 48 | 42 | 39 | 45 |
| Appearance | Clear | Hazy | Clear | Clear | Clear | Clear |

EXAMPLE 8

Formulation 24 was prepared essentially according to the procedure set forth in Example 2.

| Ingredient | Composition 24 (%) |
|---|---|
| MgLS[1] | 19.44 |
| NaAES | 3.22 |
| NaMES | 7.12 |
| LMMEA | 4.05 |
| Ethanol | 5.0 |
| MgO | 0.05 |
| Surfactant, % | 33.8 |
| Appearance | Clear |
| Performance (mini-plates) | 48 |

[1]magnesium lauryl sulfate

EXAMPLE 9

Formulation 25

Into a suitable vessel equipped with heating, cooling and mixing capabilities were added distilled water and $MgCl_2.6H_2O$. This was mixed until all of the magnesium salt had dissolved at which time Steol CA-460, sulfonated methyl ester and amide were added, and the temperature of the mixture was raised to about 140°–145° F. to completely melt the amide. The mixture was then cooled to about 90° F. and the pH adjusted as necessary to a value between 6.0 to 7.0 with citric acid or magnesium oxide.

| | % active (by weight) |
|---|---|
| Steol CA-460 | 21.0 |
| Alpha Step $NH_4$-MC-48[1] | 7.0 |
| Ninol LMP | 4.0 |
| $MgCl_2.6H_2O$ | 14.2 |
| MgO | 0.03 |
| DI Water | Q.S. to 100 |
| Performance | 45 |

[1]54.27% aqueous solution of ammonium alpha-sulfonated methyl ester of fatty acids having an average of 12 to 14 carbon atoms where the average carbon chain length is 13.6 carbon atoms.

EXAMPLE 10

Formulation 26

Into a suitable vessel equipped with heating, cooling and mixing capabilities were added water and Bio-Soft S-100. The composition was mixed until uniform at which time MgO was added. Steol CA-460 and MC-48 were added and mixed well. The mixture was heated to 140°–145° F. and Ninol LMP was added and allowed to melt completely. The mixture was cooled to 90° F. and alcohol added and the pH was adjusted as necessary to 6.0–7.0 with MgO or citric acid.

| | % active |
|---|---|
| Water DI | Q.S. to 100.00 |
| Bio-Soft S-100[1] | 18.1 |
| MgO | 1.45 |
| Alpha-Step $NH_4MC$-48 | 7.1 |
| Steol CA-460 | 3.22 |
| Ninol LMP | 4.05 |
| Ethanol 3A | 5.0 |
| Citric Acid (50%) | Q.S. |
| Performance | 51 |

[1]linear alkyl benzene sulfonic acid (LAS) with an alkyl portion having an average of 11.6 carbon atoms.

EXAMPLE 11

FORMULATIONS 26–31

The following formulations (27–32) were prepared essentially according to the teachings of PCT publications WO 92/06156 and WO 92/06161 (amounts are in weight-percent of total compostion).

| Ingredient (% aqueous) | 27 | 28 | 29 | 30 | 31 | 32 |
|---|---|---|---|---|---|---|
| DI Water | Q.S. to 100 | Q.S. to 100 | Q.S. to 100 | Q.S. to 100 | Q.S. to 100 | Q.S. to 100 |
| Glucamides 75:25 ratio of $C_{12}$:$C_{14}$ alkyl N-methyl glucamides | 5.0 | 12.5 | 10.0 | 12.5 | 10.0 | 15.0 |
| Na LAS (60%) | 25.0 | | | | | |
| Steol CA-130 (30%) | 33.3 | 38.0 | 20.7 | 38.0 | 20.7 | 13.8 |
| $NH_4$LAS (49.21%) | | 20.32 | 27.4 | 20.3 | 27.4 | 24.4 |
| Amphosol CA[1] (30%) | 6.7 | 13.3 | 6.7 | 13.3 | 6.7 | |
| Cetyl dimethyl Betaine (33%) | | 10.6 | 7.6 | 10.6 | 7.6 | 9.1 |
| Ammonyx LO[2] (30%) | | | 10.0 | | 10.0 | 16.7 |
| LMMEA | 2.0 | 3.8 | | 3.8 | | |
| Ninol 40 CO[3] | 2.0 | | | | | |
| SCS[4] (45%) | 6.7 | 2.2 | 4.4 | 2.2 | 4.4 | 6.7 |
| Ethanol 3A | 4.0 | 2.0 | | 2.0 | | 1.34 |
| MgO | 2.0 | | | | | |
| $Mg(OH)_2$ | | 1.5 | 1.5 | | | |
| EGDS[5] | | | | | | 1.0 |
| Urea | | | 0.7 | | 0.7 | |
| % Surfactant | 39.0 | 43.7 | 39.2 | 46.2 | 39.2 | 43.2 |
| Mini-plates washed | 33 | 42 | 27 | 40.5 | 33 | 30 |
| Appearance | Clear | Sl. Trans. | Cloudy | Cloudy | Cloudy | Cloudy |
| pH | 6.9 | 6.8 | 6.7 | 6.8 | 6.8 | 6.8 |

[1]30% aqueous cocoamidopropyl betaine.
[2]30% aqueous amine oxide having an average of 12 carbon atoms.
[3]Coconut monoethanol amide.
[4]Sodium cumine sulfonate.
[5]Ethylene glycol distearate.

EXAMPLE 12

The following formulations were prepared essentially according to PCT publications WO 92/06156 and WO 92/06161 (amounts are in weight-percent of total compostion).

| | 33 | 34 | 35 | 36 | 37 |
|---|---|---|---|---|---|
| 75:25 ratio of $C_{12}$:$C_{14}$ glucamide | 10.0 | 5.0 | 10.0 | 4.0 | 12.5 |
| Na MC-48 (36.34%) | 41.3 | 41.3 | 41.3 | 41.3 | 13.7 |
| Coconut acid alkyl polyglycoside (Glucopon 625) (50%) | | 30.0 | | 30.0 | |
| Mg MC-48 (37.0%) | | | | | |
| $C_{14-18}$ alpha-olefin sulfonate (40%) | | | | | 25.0 |
| Neodol 91-8[1] | | | | | 4.0 |
| Amphosol CA (30%) | 10.0 | | 10.0 | | |
| Cetyl dimethyl Betaine (33%) | | 15.2 | | 15.2 | |
| Ammonyx LO (30%) | | | | | 10.0 |
| Ninol LMP | | | | | 2.0 |
| Ninol 40CO | | | | | 2.0 |
| SCS[2] (45%) | 11.1 | 4.4 | 11.1 | 4.4 | 8.9 |
| Ethanol | | 2.2 | | 3.2 | |
| $MgCl_2$ | 0.80 | 1.90 | 0.80 | 1.90 | |
| DI Water | | Q.S. to 100% | | | |
| Mini-plates washed | 36 | 39 | 39 | 39 | 45 |
| pH | 7.5 | 6.6 | 6.2 | 6.5 | 10.3 |
| Surfactant | 33 | 42 | 32 | 41 | 40.5 |
| Appearance | Clear | Clear | Clear | Clear | Hazy |

[1]$C_9$–$C_{11}$ fatty alcohol with 8 moles of ethylene oxide.
[2]Sodium cumine sulfonate

EXAMPLE 13

A highly concentrated detergent composition (Formulation 38) was prepared as follows:

| | |
|---|---|
| Water, DI | Q.S. to 100.00 |
| Bio-Soft S-100 | 33.80 |
| MgO | 2.60 |
| Alpha-Step MC-48 | 11.34 |
| Steol CA-460 | 5.15 |
| Ninol LMP | 3.9 |
| Ethanol 3A | Q.S. |
| Citric Acid | Q.S. |

The resulting formulation contained 56.79% surfactant, and was a pasty solution having an opaque appearance.

EXAMPLE 14

To a suitable vessel equipped with heating, cooling and mixing means were added distilled water and magnesium chloride. To this mixture was then added magnesium lauryl ethoxy (3) sulfate (Mg Laureth (3) sulfate) and α-sulfonated methyl ester (MC-48); the mixture was mixed until uniform and then heated to about 140°–145° F. At 140°–145° F., amide was added and allowed to melt completely. The composition was mixed thoroughly and the pH adjusted to 6.2 to 6.8 with citric acid or magnesium oxide.

| | Formulation 39 % (Active) |
|---|---|
| Water DI | Q.S. to 100.00 |
| Mg Laureth (3) Sulfate[1] | 28.0 |
| Alpha Step MC-48 | 8.8 |
| Ninol LMP | 5.0 |
| $MgCl_2$ | 2.0 |
| MgO | Q.S. |
| Citric Acid | Q.S. |
| Mini-plates washed | 51 |

[1]magnesium salt of ethoxylated lauryl sulfate having an average of 3 moles of ethylene oxide.

EXAMPLE 15

Formulations 40 through 42 were prepared essentially according to the procedures set forth in Example 2.

| | 40 % | 41 % | 42 % |
|---|---|---|---|
| MgLAS | 24.0 | 24.0 | 24.0 |
| Steol CA-460 | 4.0 | 4.0 | 4.0 |
| Alpha-step MC-48[1] | 8.8 | 4.4 | 2.3 |
| Alpha-step MC-48[2] | — | 4.4 | 5.8 |
| Ninol LMP | 5.0 | 5.0 | 5.0 |
| Ethanol 3A | 5.0 | 5.0 | 5.0 |
| MgO | 0.05 | 0.05 | 0.05 |
| D.I. Water | — | — | — |
| p.H. | Q.S. to 100.00 | Q.S. to 100.00 | Q.S. to 100.00 |
| Mini Plates Washed | 57 | 51 | 45 |
| % surfactant | 41.8 | 41.8 | 41.8 |
| Appearance | clear | clear | hazy |
| Ratio of monosalt to di-salt in final composition | 9:1 | 4.5:1 | 2.25:1 |

[1]ratio of mono-sodium salt to di-sodium salt is about 9:1
[2]Pure di-sodium salt (98% Active)

EXAMPLE 16

Formulations 43–49 were prepared essentially according to the procedures set forth in Example 2.

| | 43 % | 44 % | 45 % | 46 % | 47 % | 48 % |
|---|---|---|---|---|---|---|
| D.I. Water | Q.S. to 100% | Q.S. to 100% | Q.S. to 100% | Q.S. to 100% | Q.S. to 100% | Q.S. to 100% |
| MgLAS (50%) | 48.0 | 48.0 | 48.0 | 48.0 | 48.0 | 48.0 |
| Steol CA-460 (60%) | 6.6 | 6.6 | 6.6 | 6.6 | 6.6 | 6.6 |
| Na alkyl sulfate (average of 8 carbon atoms) (39.6%) | 22.3 | — | — | — | — | — |
| Na alkyl ether sulfate (average of 8 carbon atoms and 1 mole of ethylene oxide (EO)) (42.3%) | — | 20.8 | — | — | — | — |
| Na alkyl ether sulfate (average of 8 carbon atoms and 2 EO) (40.2%) | — | — | 21.9 | — | — | — |
| Na alkyl sulfate (average of 10 carbon atoms) (38.5%) | — | — | — | 22.8 | — | — |
| Na alkyl ether sulfate (average of 10 carbon atoms and 1 EO) (45.8%) | — | — | — | — | 19.2 | — |
| Na alkyl ether sulfate (average of 10 carbon atoms and 2 EO) (34.1%) | — | — | — | — | — | 25.8 |
| Ninol LMP | 5.0 | 5.0 | 5.0 | 5.0 | 5.0 | 5.0 |
| Ethanol 3A | 5.0 | 5.0 | S.o | 5.0 | 5.0 | 5.0 |
| Citric Acid 50% | Q.S. | Q.S. | Q.S. | Q.S. | Q.S. | Q.S. |

-continued

| | 43 % | 44 % | 45 % | 46 % | 47 % | 48 % |
|---|---|---|---|---|---|---|
| MgO | Q.S. | Q.S. | Q.S. | Q.S. | Q.S. | Q.S. |
| Mini Plates Washed | 42 | 45 | 48 | 48 | 45 | 54 |
| Appearance (as is) | Clear | Clear | Clear | Clear | Clear | Clear |

Each of the above formulations above had a hazy or turbid appearance prior to the addition of 3A Alcohol.

From the foregoing it will be appreciated that, although specific embodiments of the invention have been described herein for purposes of illustration, various modifications may be made without deviating from the spirit and scope of the invention.

What is claimed is:

1. A detergent composition comprising:

(a) about 5 to 10% by weight of a salt of an alpha-sulfonated methyl ester of a fatty acid having an average of from about 12–14 carbon atoms;

(b) about 2 to 10% by weight of alkyl ethoxy sulfate having a degree of ethoxylation of about 3;

(c) about 17 to 25% by weight of linear alkyl benzene sulfonate having an alkyl chain of 10–13 carbon atoms;

(d) about 1–6% by weight of a nonionic surfactant; and (e) from about 0.02 to 0.1M of magnesium ion.

2. A detergent composition according to claim 1, where the salt of an alpha-sulfonated methyl ester of a fatty acid is a blend of an alpha-sulfonated methyl ester of a fatty acid having an average of from about 12–14 carbon atoms and a salt of a alpha-sulfonated carboxylic acid having an average of from about 12–14, where the molar ratio of methyl ester to sulfonated carboxylic acid is at least about 2:1.

3. A detergent composition comprising:

(a) about 7 to 8% by weight of a salt of an alpha-sulfonated methyl ester of a fatty acid having an average of from about 12–14 carbon atoms;

(b) about 3 to 5% by weight of alkyl ethoxy sulfate having a degree of ethoxylation of about 3;

(c) about 17 to 25% by weight of linear alkyl benzene sulfonate having an alkyl chain of 10–13 carbon atoms;

(d) about 3–5% by weight of a fatty acid alkanolamide; and (e) from about 0.02 to 0.1M of magnesium ion.

4. A method for preparing a detergent composition comprising:

(a) preparing a surfactant mixture to comprise about 5 to 10% by weight of an alpha-sulfonated methyl ester of a fatty acid having an average of about 13.6 carbon atoms;

about 2 to 10% by weight of lauryl ethoxy sulfate having a degree of ethoxylation of about 3;

about 17 to 25% by weight of linear alkyl benzene sulfonate having an alkyl chain of 10–13 carbon atoms; and about 1–6% of a fatty acid alkanolamide; and (b) adding a magnesium salt in an amount such that the concentration of magnesium ion in the detergent composition is from about 0.02 to 0.1M.

* * * * *